US012697160B2

(12) United States Patent (10) Patent No.: US 12,697,160 B2

Ogawa et al. (45) Date of Patent: Aug. 4, 2026

(54) TREATMENT PORTION OF MEDICAL ENERGY DEVICE, MANUFACTURING METHOD THEREFOR, AND MEDICAL ENERGY DEVICE

(71) Applicant: OLYMPUS CORPORATION, Tokyo (JP)

(72) Inventors: Yoshiyuki Ogawa, Hachioji (JP); Hiroaki Kasai, Hachioji (JP); Takuya Fujihara, Hachioji (JP); Yu Murano, Hachioji (JP); Issei Maeda, Hachioji (JP); Asuka Tachikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 419 days.

(21) Appl. No.: 18/218,856

(22) Filed: Jul. 6, 2023

(65) Prior Publication Data

US 2023/0355291 A1 Nov. 9, 2023

Related U.S. Application Data

(63) Continuation of application No. PCT/JP2021/008221, filed on Mar. 3, 2021.

(51) Int. Cl.
*A61B 18/04* (2006.01)
*A61B 17/00* (2006.01)
*A61B 18/00* (2006.01)

(52) U.S. Cl.
CPC .... *A61B 18/04* (2013.01); *A61B 2017/00526* (2013.01); *A61B 2018/0013* (2013.01);
(Continued)

(58) Field of Classification Search
CPC .. A61B 2018/0013; A61B 2018/00595; A61B 2018/00601; A61B 18/1445
See application file for complete search history.

(56) References Cited

U.S. PATENT DOCUMENTS 5,702,387 A 12/1997 Arts et al.
2006/0259032 A1* 11/2006 Nesbitt .............. A61B 18/1402
606/49

(Continued)

FOREIGN PATENT DOCUMENTS

JP 3182153 B2 7/2001
JP 2003-524500 A 8/2003

(Continued)

OTHER PUBLICATIONS

Manufacturer data sheet on silicone rubber vs silicone resin: "What is the difference between silicone resin and silicone rubber?", Author & publication date unknown but accessed on Sep. 24, 2025.*

(Continued)

*Primary Examiner* — Thomas A Giuliani
*Assistant Examiner* — Abigail M Ziegler
(74) *Attorney, Agent, or Firm* — Scully, Scott, Murphy & Presser, P.C.

(57) ABSTRACT

This treatment portion of a medical energy device treats a biological tissue by transferring energy to the biological tissue, in a state where the treatment portion is in contact with the biological tissue. The treatment portion of the medical energy device includes a main body portion and a covering film. The main body portion transfers energy to the biological tissue. The covering film contains silicone as a main component, and covers the surface of the main body portion. The silicone includes at least a D unit and a T unit. In the silicone, the molar ratio of silicon atoms forming the D unit with respect to all the silicon atoms is 40-99%. In the silicone, the molar ratio of methyl functional groups bonded to the silicon atoms with respect to all functional groups bonded to the silicon atoms is at least 60%.

10 Claims, 2 Drawing Sheets

(52) U.S. Cl.
    CPC .............. *A61B 2018/00595* (2013.01); *A61B*
                            *2018/00601* (2013.01)

(56)                References Cited

U.S. PATENT DOCUMENTS

| | | | | |
|---|---|---|---|---|
| 2018/0280075 | A1 * | 10/2018 | Nott ................... | A61B 18/1445 |
| 2019/0192212 | A1 * | 6/2019 | Murano ................. | B32B 27/20 |
| 2020/0164115 | A1 * | 5/2020 | Murano .................. | A61L 31/14 |
| 2020/0205880 | A1 * | 7/2020 | Kasai ................ | A61B 18/1402 |
| 2021/0307809 | A1 * | 10/2021 | Yorozu ................. | C08G 77/20 |
| 2022/0110673 | A1 * | 4/2022 | Boronyak .......... | A61B 18/1445 |
| 2024/0081892 | A1 * | 3/2024 | Batchelor .......... | A61B 18/1445 |

FOREIGN PATENT DOCUMENTS

| | | | | | |
|---|---|---|---|---|---|
| JP | 2018-075303 | A | | 5/2018 | |
| JP | 2020-080995 | A | | 6/2020 | |
| WO | 2001/064122 | A1 | | 9/2001 | |
| WO | WO-2019078089 | A1 * | 4/2019 | ......... | A61B 18/1402 |
| WO | WO-2019082765 | A1 * | 5/2019 | ............ | A61B 18/14 |
| WO | WO-2021161785 | A1 * | 8/2021 | ............ | A61B 18/14 |

OTHER PUBLICATIONS

Manufacturer data sheet for KR-251 (Year: 2016) accessed on Sep. 24, 2025.*
International Search Report May 18, 2021 received in PCT/JP2021/008221.

* cited by examiner

TREATMENT PORTION OF MEDICAL ENERGY DEVICE, MANUFACTURING METHOD THEREFOR, AND MEDICAL ENERGY DEVICE

CROSS-REFERENCE TO RELATED APPLICATIONS

The present application is a continuation application based on PCT Patent Application No. PCT/JP2021/008221, filed on Mar. 3, 2021, the entire content of which is hereby incorporated by reference.

BACKGROUND

Technical Field

The present invention relates to a treatment portion of a medical energy device, a manufacturing method thereof, and a medical energy device.

Description of the Background

A configuration is known in which a silicone film is formed on a surface of a metal base material in a treatment portion of a medical energy device. For example, Japanese Unexamined Patent Application, First Publication No. 2018-75303 (hereinafter referred to as Patent Document 1) describes, as an example of a medical energy device, a high-frequency knife in which a silicone resin film containing a conductive material is formed on a surface of a metal electrode portion.

The treatment portion in the medical energy device performs treatments such as incision, cauterization, and coagulation of a biological tissue by heating the biological tissue in a state where the treatment portion is in contact with the biological tissue. By repeated treatments, repeated temperature loads occur in the treatment portion.

For example, in the treatment portion in the medical energy device exemplified in Patent Document 1, a silicone resin film is formed on a surface of a metal electrode section. In this case, repeated thermal stress is generated in the silicone resin film due to the difference in thermal expansion coefficient between the electrode portion and the silicone resin film. As a result, cracks occur in the silicone resin film, and the silicone resin film peels off from the electrode portion. When such cracks or peeling occur, the biological tissue tends to adhere to the treatment portion, and treatment performance is lowered or treatment becomes difficult.

In recent years, in order to improve the treatment performance, there is a strong demand for the treatment to be performed while the temperature of the treatment portion is raised to a higher temperature. For example, in the case of a silicone resin film, especially when treatment is repeated at a high temperature of 300° C. or higher, cracks, peeling, and the like are likely to occur, and the service life of the treatment portion may be shortened.

SUMMARY

The present invention provides a treatment portion of a medical energy device, a manufacturing method thereof, and a medical energy device, which improve durability in repeated treatments.

A first aspect of the present invention is a treatment portion of a medical energy device that treats a biological tissue by transferring energy to the biological tissue, in a state where the treatment portion is in contact with the biological tissue. The treatment portion includes: a main body portion that transfers the energy to the biological tissue; and a covering film that contains silicone as a main component and covers a surface of the main body portion. The silicone includes at least a D unit and a T unit, in the silicone, a molar ratio of silicon atoms forming the D unit with respect to all the silicon atoms is 40% or more and 99% or less, and in the silicone, a molar ratio of methyl functional groups bonded to the silicon atoms with respect to all functional groups bonded to the silicon atoms is 60% or more.

A second aspect of the present invention is a manufacturing method for a treatment portion of a medical energy device that treats a biological tissue by transferring energy to the biological tissue, in a state where the treatment portion is in contact with the biological tissue. The method includes: preparing a main body portion and a coating liquid, the main body portion transferring energy to the biological tissue, the coating liquid containing silicone including at least a D unit and a T unit and forming a polymer in which a molar ratio of the silicon atoms forming the D unit with respect to all the silicon atoms is 40% or more and 99% or less, and a molar ratio of methyl functional groups bonded to the silicon atoms with respect to all functional groups bonded to the silicon atoms is 60% or more; applying the coating liquid to a surface of the main body portion; and forming a covering film which contains the silicone as a main component and covers the surface of the main body portion by heating and curing the applied coating liquid.

A third aspect of the present invention is a medical energy device including the treatment portion according to the first aspect.

According to the treatment portion of the medical energy device of the first aspect, the manufacturing method for the treatment portion of the medical energy device of the second aspect, and the medical energy device of the third aspect, durability in repeated treatments can be improved.

DETAILED DESCRIPTION

Embodiments

The treatment portion of the medical energy device of the embodiment of the present invention and the manufacturing method thereof will be described below with reference to the accompanying drawings.

Figures 1, 2:
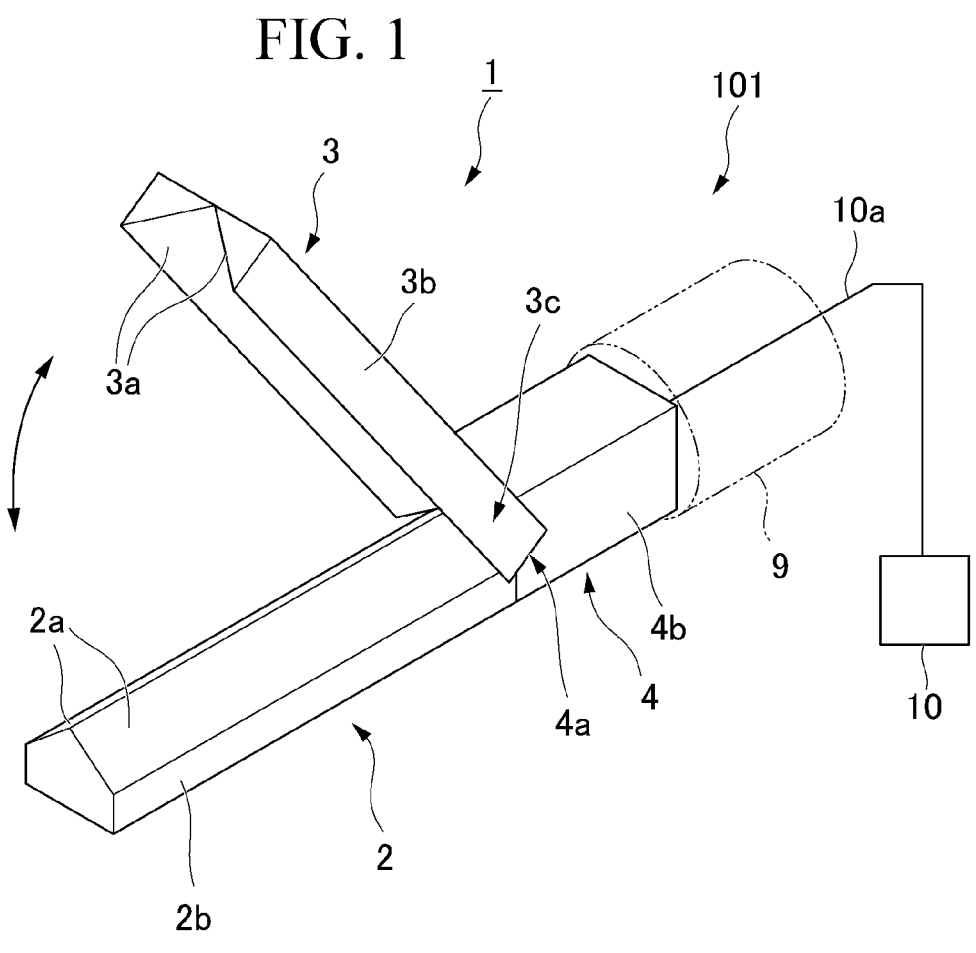
FIG. 1 is a schematic perspective view showing an example of a treatment portion of a medical energy device according to an embodiment of the present invention.
FIG. 2 is a schematic cross-sectional view of the treatment portion of the medical energy device according to the embodiment of the present invention.

FIG. 1 is a schematic perspective view showing an example of a treatment portion of a medical energy device according to an embodiment of the present invention. FIG. 2 is a schematic cross-sectional view of the treatment portion of the medical energy device according to the embodiment of the invention.

A medical energy device 101 of this embodiment shown in FIG. 1 is an example of a medical device that transfers energy to a biological tissue to treat the biological tissue in a state where the medical device is in contact with the biological tissue.

The type of treatment is not particularly limited as long as it is a treatment realized by transferring energy to the biological tissue in a state where the medical device is in contact with the biological tissue. The type of treatment is, for example, cutting, excision, coagulation (hemostasis), cauterization, or the like of the biological tissue. Such a treatment is realized, for example, by raising the temperature of the biological tissue to a temperature at which water in the biological tissue evaporates or proteins in the biological tissue denature.

The type of energy transferred to the biological tissue is not particularly limited in order to bring the biological tissue to a high-temperature state. The type of energy is, for example, electrical energy, ultrasonic vibration energy, thermal energy, or the like. The energy transferred to the biological tissue is not limited to one type, and a plurality of types of energy may be transferred.

The specific type of the medical energy device is, for example, a high-frequency knife, a high-frequency scissor-type knife, an electric scalpel, a snare, an ultrasonic coagulation and incision device, a high-frequency cauterization device, a high-frequency/ultrasonic mixing device, and a heating cauterization heater.

The medical energy device 101 includes a holder 9, a treatment portion 1, and a power supply 10.

The holder 9 is a member that supports the treatment portion 1. The holder 9 may have a shape that can be held by an operator's hand, for example. The holder 9 may have a shape that can be held by a medical robot, for example. The holder 9 may be fixed to a medical robot, for example. The holder 9 is a part placed outside a patient's body and is not used in contact with the biological tissue to be treated.

In the example shown in FIG. 1, the holder 9 is shaped like a rod so as to be capable of being held by an operator or a medical robot.

The treatment portion 1 has an appropriate shape capable of transferring energy necessary for treatment in a state where the treatment portion is in contact with the biological tissue.

In the example shown in FIG. 1, the treatment portion 1 can transfer one or both of ultrasonic vibration energy and high-frequency electrical energy to the biological tissue.

The treatment portion 1 includes a support member 4, a first gripping portion 2, and a second gripping portion 3.

The support member 4 is fixed to the end of the holder 9. In this embodiment, the support member 4 is a rod-shaped member.

The shape of the support member 4 is not particularly limited. The outer shape of the support member 4 shown in FIG. 1 is, for example, a quadrangular prism having four side surfaces 4b on the sides in the extending direction. A wiring 10a connected to a power supply 10, as described later, is inserted through the support member 4. The wiring 10a is inserted inside the holder 9. The wiring 10a extends from the end of the holder 9 to the outside of the holder 9. The length of the support member 4 is such that the treatment portion 1 can be placed near the treatment target inside the patient's body while the holder 9 is held outside the patient's body.

The temperature of the supporting member 4 may rise in the vicinity of a first gripping portion 2 and a second gripping portion 3 described later due to heat conduction from the first gripping portion 2 and the second gripping portion 3. The support member 4 in the vicinity of the first gripping portion 2 and the second gripping portion 3 may come into contact with the biological tissue to be treated. For this reason, each side surface 4b of the support member 4, at least in the vicinity of the first gripping portion 2 and the second gripping portion 3, is preferably coated with an anti-adhesion film that prevents the adhesion of the biological tissue.

In this embodiment, the support member 4 includes a base material 40 (main body portion) and a covering film 5, as in FIG. 2 showing a cross-sectional configuration near the side surface 4b.

The base material 40 may be made of, for example, metal, ceramic, resin, or a composite material thereof.

Examples of a metal that can be suitably used for the base material 40 include, for example, stainless steel, aluminum, aluminum alloys, titanium, titanium alloys, or the like.

Examples of ceramics that can be suitably used for the base material 40 include, for example, aluminum nitride, silicon nitride, and alumina (aluminum oxide).

The covering film 5 on the support member 4 covers the surface 40a of the base material 40. A detailed configuration of the covering film 5 will be described after the treatment portion 1 is described.

As shown in FIG. 1, at the side surfaces 4b facing each other at the ends of the support member 4 in the extending direction, a rotation support portion 4a is provided between the side surfaces 4b and the second gripping portion 3, as described later. The rotation support portion 4a supports rotation of the second gripping portion 3, as described later, about an axis orthogonal to the extending direction.

The configuration of the rotation support portion 4a is not particularly limited as long as it can support rotation of the second gripping portion 3, as described later. For example, the rotation support portion 4a may include a rotation support shaft or a shaft bearing.

Although not shown, an operation member for controlling the amount of rotation of the second gripping portion 3 described later is inserted through the inside of the support member 4. The operation member extends inside the holder 9 and is connected to an operation portion (not shown) of the holder 9. For example, as the operating member, an operating wire, an operating rod, or the like that advances and retracts in the longitudinal direction of the support member 4 may be used.

One or both of the first gripping portion 2 and the second gripping portion 3 are fixed to the support member 4 so as to be movable relative to each other so that the biological tissue can be gripped during treatment thereof.

In the example shown in FIG. 1, the first gripping portion 2 is a rod-shaped body that protrudes forward from the distal end of the supporting member 4. A proximal end portion of the first gripping portion 2 in the longitudinal direction is fixed to the support member 4 with a piezoelectric element arranged in the support member 4 interposed therebetween.

The piezoelectric element is a vibration source that ultrasonically vibrates the first gripping portion 2. The piezoelectric element is electrically connected to a vibration control terminal of the power supply 10 through the wiring 10a. A driving signal for ultrasonically oscillating the piezoelectric element is supplied from a vibration control terminal of the power supply 10, as described later.

The second gripping portion 3 is rotatably supported by the rotation support portion 4a of the support member 4.

In this embodiment, the first gripping portion 2 and the second gripping portion 3 are electrically connected to a high-frequency output terminal of the power supply 10, as described later, through the wiring 10a. High-frequency power is supplied from the high-frequency output terminal through the first gripping portion 2 and the second gripping portion 3 to perform high-frequency treatment on the biological tissue that is in contact with the first gripping portion 2 and the second gripping portion 3.

The surface of the first gripping portion 2 includes a first gripping surface 2a that contacts the biological tissue, and an outer surface 2b excluding the first gripping surface 2a.

The shape of the first gripping portion 2 is not particularly limited. In the present embodiment, the first gripping portion 2 is, for example, a pentagonal prism having a shape in which a convex pentagonal shape is pushed out in the extending direction. The first gripping surface 2a extends in the extending direction of the pentagonal prism and includes two side surfaces that are adjacent to each other in the circumferential direction. Each first gripping surface 2a forms a triangular cross-sectional ridge extending in the extension direction.

FIG. 2 shows a cross-sectional configuration near the first gripping surface 2a and the outer surface 2b. The first gripping portion 2 includes a base material 20 (main body portion) and the covering film 5.

The base material 20 may be made of, for example, metal, ceramic, or a composite material thereof. For example, when the base material 20 is made of ceramic, it is more preferable that the first gripping portion 2 further include a metal electrode (not shown) coated with the base material 20.

Examples of the metal that can be suitably used for the base material 20 include, for example, stainless steel, aluminum, aluminum alloys, titanium, titanium alloys, or the like.

Examples of ceramics that can be suitably used for the base material 20 include, for example, aluminum nitride, silicon nitride, alumina (aluminum oxide), or the like.

The wiring 10a connected to the high-frequency output terminal is connected to the base material 20 when the base material 20 is metal, and to the metal electrode when the base material 20 is non-metal and covers the metal electrode.

The covering film 5 on the first gripping portion 2 covers the surface 20a of the base material 20. A detailed configuration of the covering film 5 will be described after the treatment portion 1 is described.

As shown in FIG. 1, the second gripping portion 3 is a rod-shaped body provided for the purpose of gripping the biological tissue with the first gripping surface 2a of the first gripping portion 2.

A connecting portion 3c is formed at the end of the second gripping portion 3 in the longitudinal direction.

The connecting portion 3c is rotatably connected to the rotation support portion 4a of the support member 4. For example, when the rotation support portion 4a has a rotation support shaft, the connecting portion 3c may be configured by a groove, a hole, a shaft bearing, or the like that can rotate about the rotation support shaft. For example, when the rotation support portion 4a has a shaft bearing, the connecting portion 3c may be configured by a shaft, projection, or the like that engages with the shaft bearing.

In this embodiment, the connecting portion 3c and the rotation support portion 4a are electrically insulated from each other.

Although not shown, a connecting portion that connects with the above-described operating member is formed in the vicinity of the connecting portion 3c. For example, when the operating member advances and retracts, the connecting portion transfers the movement of the operating member to the second gripping portion 3. The moment of the operating force acting on the connecting portion causes the second gripping portion 3 to rotate around the rotation support portion 4a.

At least one of the operating member and the connecting portion is not electrically connected to the wiring 10a, which is connected to the second gripping portion 3.

The shape of the second gripping portion 3 is not particularly limited as long as the object to be treated can be gripped between the second gripping portion 3 and the first gripping portion 2. In the example shown in FIG. 1, the second gripping portion 3 is a rod-shaped body having approximately the same length as the first gripping portion 2.

The surface of the second gripping portion 3 includes a second gripping surface 3a that contacts the object to be treated, and an outer surface 3b that excludes the second gripping surface 3a.

The second gripping surface 3a includes two planes adjacent to each other. The second gripping surface 3a forms a V-shaped groove extending in the longitudinal direction of the second gripping portion 3.

In this embodiment, the shape of the V-shaped groove is a concave shape corresponding to the convex shape of the first gripping surface 2a of the first gripping portion 2. When the second gripping portion 3 is turned parallel to the first gripping portion 2 (hereinafter referred to as the closed state), the second gripping surface 3a and the first gripping surface 2a of the first gripping portion 2 are parallel to each other. The distance between the first gripping surface 2a and the second gripping surface 3a facing each other in the closed state is not particularly limited as long as it is 0 mm or more and smaller than the thickness of the object to be treated.

However, if the first gripping surface 2a can enter the inside of the V-shaped groove when the second gripping portion 3 is brought closer to the first gripping portion 2 by turning, the angle formed by each first gripping surface 2a and the angle formed by each second gripping surface 3a may be different from each other.

The second gripping portion 3 includes a base material 30 (main body portion) and the covering film 5, as in FIG. 2 showing the cross-sectional configuration near the second gripping surface 3a and the outer surface 3b.

The base material 30 may be made of, for example, metal, ceramic, or a composite material thereof. For example, when the base material 30 is made of ceramic, the second gripping portion 3 preferably further includes metal electrodes (not shown) covered with the base material 30.

Examples of metals and ceramics that can be suitably used for the base material 30 are the same as those for the base material 20 described above.

The wiring 10a, which is connected to the high-frequency output terminal, is connected to the base material 30 when the base material 30 is metal, and is connected to the metal electrode when the base material 30 is non-metal covering the metal electrode.

The covering film 5 on the second gripping portion 3 covers the surface 30a of the base material 30. A detailed configuration of the covering film 5 will be described after the treatment portion 1 is described.

As shown in FIG. 1, the power supply 10 is electrically connected to the treatment portion 1 through the wiring 10a. The power supply 10 includes a vibration control terminal, a high-frequency output terminal, and a power supply circuit that outputs electrical signals to these terminals. A drive signal for ultrasonically oscillating the piezoelectric element to which the first gripping portion 2 is connected is output to the vibration control terminal. High-frequency power to be applied to the first gripping portion 2 and the second gripping portion 3 is output to the high-frequency output terminal.

In the treatment portion 1, the first gripping portion 2 and the second gripping portion 3 are examples of main body portions that transfer energy to the biological tissue. The support member 4 is not intended to transfer energy to the biological tissue, but is an example of a main body portion when there is a possibility of contacting and transferring energy to the biological tissue during treatment.

Next, the covering film 5 will be described.

The covering film 5 is provided mainly for the purpose of suppressing adhesion of the biological tissue to the treatment portion 1. The covering film 5 may be provided on any member and part in the treatment portion 1 as long as they are likely to come into contact with the biological tissue.

As shown in FIG. 2, in the present embodiment, the covering film 5 is formed on at least the first gripping surface 2*a* and the outer surface 2*b* of the first gripping portion 2, the second gripping surface 3*a* and the outer surface 3*b* of the second gripping portion 3, and the side surface 4*b* of the support member 4.

The main component of the covering film 5 is silicone. The covering film 5 covers each surface of the base materials 20, 30, and 40.

Since silicone has excellent water repellency and heat resistance, silicone is sometimes used as an anti-adhesion film on the surface of the treatment portion. However, it is known that repeated treatments result in a gradual decline in treatment performance.

According to the observation by the inventor of the present application, in the treatment portion with degraded treatment performance, the biological tissue adheres to the part where the silicone film has cracked or peeled off from the main body portion. Such deterioration is particularly apparent when the temperature of the silicone film had been 300° C. or higher. The inventor of the present application believes that the cracking and peeling of the silicone film are caused by the internal stress caused by the difference in thermal expansion coefficient between the main body portion and the silicone film, and as a result of intensive research into internal stress buffering means, the inventor has found a new buffering means and has arrived at the present invention.

Silicone is an organosilicon compound with a siloxane bond as a main skeleton. Silicone is formed by combinations of an M unit, a D unit, a T unit, and a Q unit.

In the M unit, one oxygen atom and three functional groups are bonded to one silicon atom. Since the atomic group of the M unit shares an oxygen atom with other adjacent units, the atomic group of the M unit is represented as $R_3SiO_{1/2}$ wherein R is an organic functional group.

In the D unit, two oxygen atoms and two functional groups are bonded to one silicon atom. The atomic group of the D unit is represented as $R_2SiO_{2/2}$.

In the T unit, three oxygen atoms and one functional group are bonded to one silicon atom. The atomic group of the T unit is represented as $R_1SiO_{3/2}$.

In the Q unit, four oxygen atoms are bonded to one silicon atom. The atomic group of the Q unit is represented as $SiO_{4/2}$.

By including a methyl functional group ($CH_3$—) as the functional group, the water repellency becomes remarkable, so the adhesion prevention performance of the biological tissue can be improved. A phenyl group ($C_6H_5$—) is also suitable as the functional group.

For example, as other functional groups, an ethyl group, a propyl group, an amino group, or the like may be included.

The properties of silicone as a whole change when the M unit, the D unit, the T unit, and the Q unit are bonded to each other in various ratios. Specifically, an oxygen atom is shared by two silicon atoms, so as to serve as a "hand" that connects the two silicon atoms. Therefore, the Q unit has 4 hands, the T unit has 3 hands, the D unit has 2 hands, and the M unit has 1 hand. For example, when there are many Q units, since each Q unit has four arms, the three-dimensional network structure becomes dominant, and a hard solid resin is formed. In contrast, when multiple D units are linked together, since each D unit has two hands, a linear structure is formed. Since this linear structure extends spirally without branching in the middle, it is rich in stretchability and flexibility.

For this reason, even in a silicone resin having a three-dimensional network structure as a whole, the part rich in D units has a higher ratio of a linear structure than a part rich in Q units, and is therefore has excellent stretchability and flexibility.

In the present embodiment, in the silicone contained in the covering film 5, the molar ratio of silicon atoms forming the D unit with respect to all the silicon atoms in the silicone is 40% or more and 99% or less, and in the silicone, the molar ratio of methyl functional groups bonded to the silicon atoms with respect to all functional groups bonded to the silicon atoms is 60% or more (the molar ratio of methyl functional groups is related to anti-adhesion performance).

Hereinafter, for the sake of simplicity, the molar ratio of silicon atoms forming the D unit to all the silicon atoms in silicone is referred to as "D unit component molar ratio". The "D unit component molar ratio" represents the ratio of the number of silicon atoms forming the D unit with respect to the total number of silicon atoms in the silicone. Similarly, the molar ratio of silicon atoms forming the T unit to all the silicon atoms in silicone is referred to as "T unit component molar ratio."

In silicone, the molar ratio of methyl functional groups bonded to silicon atoms with respect to all functional groups bonded to the silicon atoms is referred to as "methyl functional group molar ratio". The "methyl functional group molar ratio" represents the ratio of the number of methyl functional groups to the total number of functional groups bonded to all the silicon atoms of the silicone.

The D unit component molar ratio can be obtained, for example, by measuring the $^{29}$Si-NMR (nuclear magnetic resonance) spectrum of a sample of the covering film 5.

The methyl functional group molar ratio can be determined, for example, by measuring the $^{13}$C-NMR spectrum and $^1$H-NMR spectrum of a sample of the covering film 5.

When the molar ratio of the D unit component is less than 40%, the number of silicon atoms forming the T unit and the Q unit becomes relatively large, and the stretchability and flexibility of the covering film 5 are reduced, so that cracks and peeling are likely to occur due to thermal stress due to repeated treatments.

The higher the D unit component molar ratio, the better. For example, the D unit component molar ratio may be 60% or more. However, when the molar ratio of the D unit component reaches 100%, the hardness of the covering film 5 is low, and there is a possibility that it will be destroyed during treatment. For example, the experiment conducted by the inventor of the present application has revealed that the hardness of the covering film 5 is insufficient even though polydimethylsiloxane has the D unit component molar ratio of 100%. In addition, other silicone, which has a high D unit component molar ratio and provides an insufficient hardness of the covering film 5, has not been found. Therefore, it can be said that the appropriate range for the D unit component molar ratio is 40% or more and 99% or less.

When the appropriate range for the D unit component molar ratio is set to be 40% or more, it is necessary to exclude polydimethylsiloxane.

When the methyl functional group molar ratio is less than 60%, the water repellency of the covering film 5 is lowered, so the adhesion prevention performance of the covering film 5 itself against the biological tissue is lowered.

The higher the methyl functional group molar ratio, the more preferable. For example, the methyl functional group molar ratio may be 90% or more.

The thickness of the covering film 5 is preferably as thin as possible in terms of facilitating reduction of the internal stress of the covering film 5. For example, the film thickness of the covering film 5 is more preferably 60 μm or less.

When the film thickness of the covering film 5 exceeds 60 μm, the change in internal stress due to the temperature difference that accompanies repeated treatment will increase, and the covering film 5 will easily deteriorate.

The lower limit of the film thickness of the covering film 5 is not particularly limited as long as the change in internal stress can be reduced. For example, the film thickness of the covering film 5 may be 1 nm or more.

From the viewpoint of making the covering film 5 easier to manufacture, it is more preferable that the thickness of the covering film 5 be 10 μm or more.

From the viewpoint of making it easier to ensure the insulation of the covering film 5, the thickness of the covering film 5 is more preferably 20 μm or more.

When a single silicone film is formed with a thickness of more than 20 μm as the covering film 5, it is not possible to apply high-frequency power from the treatment portion 1 to the biological tissue. However, by forming a silicone film with a thickness of 20 μm or less as the covering film 5 or by blending a conductive filler into the silicone film, it is possible to apply high-frequency current from the treatment portion 1 to the biological tissue.

For example, when hemostasis is performed by high-frequency energization, there is a possibility that the surface of the treatment portion 1 that grips the biological tissue will be scorched. However, as the covering film 5, by forming a single silicone film with a thickness of 20 μm or less, or by blending a conductive filler into silicone, it is possible to prevent scorching during treatment even when used on the gripping side of the treatment portion 1.

Therefore, in the treatment portion 1 that performs a treatment that requires high-frequency electricity, it is more preferable that the covering film 5, which covers at least the first gripping surface 2*a* and the second gripping surface 3*a*, be formed by a silicone film containing conductive filler or a silicone film with a thickness of 20 μm or less that does not contain conductive filler.

Examples of the conductive filler that can be suitably used for the covering film 5 include copper, silver, alumina, tungsten, carbon, or the like.

In addition, experiments by the inventor of the present application have revealed that the volume ratio of the conductive filler to the entire covering film 5 is preferably 40% or more to 90% or less in order to obtain good conductivity.

The conductive filler may be mixed inside the covering film 5, or may be placed on the surface of the covering film 5 by coating the surface of the silicone film after forming a silicone film.

The covering film 5 may contain a hollow filler. In this case, the heat insulating property of the covering film 5 can be improved. For example, a material of the hollow filler may be alumina, silica, borosilicate alumina glass, sodium borosilicate glass, aminosilicate glass, soda lime borosilicate glass, or the like. For example, the hollow filter may be conductive filler.

The shape, vacancy rate, and the like of the hollow filler are not particularly limited as long as the covering film 5 can obtain the required heat insulation performance.

For example, in a case where the outer surfaces 2*b* and 3*b* such as the back surface of the treatment portion become too hot during treatment, the biological tissue such as an organ may be damaged when the high-temperature portions of the outer surfaces 2*b* and 3*b* come into contact with the biological tissue.

When the covering film 5 has a good heat insulating property, the heat generated during treatment is less likely to be transferred to the back surface of the treatment portion 1 or the like, so that it is possible to prevent damage to internal organs due to heat.

When the ratio of the volume of the vacant space to the volume of the covering film 5 is defined as the vacancy rate, for example, the covering film 5 has good heat insulation when the vacancy rate is 20% or more and 90% or less.

When the vacancy rate is less than 20%, the insulation may be insufficient, and when the vacancy rate exceeds 90%, the strength of the membrane may be insufficient.

Instead of containing the hollow filler in the covering film 5, air bubbles may be dispersed in the covering film 5 to form vacant spaces inside the covering film 5. Also in this case, the vacancy rate may be 20% or more and 90% or less.

When the heat insulating properties of the covering film 5 are improved by adding the hollow filler or forming the vacant space, it is preferable that the film thickness of the covering film 5 be thicker. For example, the film thickness of the covering film 5 is preferably 50 μm or more.

For example, when forming a covering film by coating a silicone resin on the ultrasonic vibrating portion that contacts the treatment target and transfers ultrasonic vibrations to the treatment target in the treatment portion 1, there is a possibility that the covering film will not be able to follow the vibration of the ultrasonic waves and will be destroyed.

However, as described later, the silicone, which is the main component of the covering film 5 in this embodiment, contains a large number of D units, so it is more flexible than ordinary silicone resin. For this reason, the covering film 5 in this embodiment is more likely to follow the ultrasonic vibrations than the silicone resin film, even when it receives the ultrasonic vibrations, so that it is less likely to be destroyed and has improved durability.

Therefore, the covering film 5 of the present embodiment is particularly suitable for the treatment portion 1 that vibrates ultrasonically.

Next, a manufacturing method for the treatment portion 1 of the medical energy device of this embodiment will be described.

In order to manufacture the treatment portion 1, the covering film 5 is formed on each surface of the base materials 20, 30, and 40 to form the first gripping portion 2, the second gripping portion 3, and the support member 4. Thereafter, the treatment portion 1 is manufactured by assembling the first gripping portion 2, the second gripping portion 3, and the support member 4.

Since the process of forming the covering film 5 on the base materials 20, 30, and 40 is common, an example of forming the covering film 5 on the base material 20 will be described below. Regarding the method of manufacturing the second gripping portion 3 and the support member 4, the base material 20 and the surface 20a below should be read as the base materials 30, 40 and the surfaces 30a, 40a, respectively.

The manufacturing process of the first gripping portion 2 includes a preparation process, a coating process, and a curing process as processes related to the covering film 5.

In the preparation process, the base material 20 and the coating liquid for forming the covering film 5 are prepared.

The surface 20a of the base material 20 prepared in this step is formed in the shape of the first gripping portion 2 without the covering film 5.

The coating liquid contains at least one type of silicone that forms a polymer. The at least one type of silicone is selected from materials that, when polymerized, have a D unit component molar ratio of 40% or more and a methyl functional group molar ratio of 60% or more.

That is, the D unit component molar ratio in the entire silicone contained in the coating liquid is greater than 40% in consideration of the decrease in D units in the polymerization reaction. Similarly, the molar ratio of methyl functional groups in the entire silicone contained in the coating liquid is greater than 60%, taking into account the reduction of methyl functional groups in the polymerization reaction.

The D unit component molar ratio in the coating liquid can be determined, for example, by measuring the $^{29}$Si-NMR (nuclear magnetic resonance) spectrum of the coating liquid sample.

The molar ratio of methyl functional groups in the coating liquid can be determined, for example, by measuring the $^{13}$C-NMR spectrum and $^{1}$H-NMR spectrum of the coating liquid sample.

When multiple types of silicones are contained in the coating liquid, the amount of D units and the amount of methyl functional groups of the silicones in the coating liquid can be adjusted by mixing the multiple types of silicones at an appropriate ratio. The amounts of D units and methyl functional groups in the multiple types of silicones are not particularly limited as long as the necessary amounts of D units and methyl functional groups are obtained after curing.

For example, the multiple types of silicones may include a first silicone having a large D unit component molar ratio in the molecule and a second silicone having a smaller D unit component molar ratio in the molecule than the first silicone. In this case, it is easy to control the amount of D units after curing by controlling the compounding ratio of the first silicone and the second silicone.

The molar ratio of methyl functional groups in each molecule of the first silicone and the second silicone is not particularly limited as long as the molar ratio of methyl functional groups in the polymer as a whole is 60% or more. From the point of easily improving the methyl functional group molar ratio, the first silicone preferably contains a methyl functional group, and more preferably both the first silicone and the second silicone contain a methyl functional group.

The first silicone is not particularly limited as long as it contains many D units. For example, polydiorganosiloxane may be used as the first silicone. It is more preferable to use polydimethylsiloxane as the first silicone in that the content of methyl functional groups in the covering film 5 can be easily increased.

The second silicone is not particularly limited as long as it contains a T unit and has a smaller molar ratio of the D unit component in the molecule compared to the first silicone.

For example, the second silicone may be free of D units. For example, the second silicone may contain Q units.

For example, as the second silicone, polyorganosilicone having a large molar ratio of silicon atoms forming T units in the silicon atoms in the molecule may be used. For example, a silicone resin or the like may be used as the second silicone. In terms of facilitating an increase in the content of methyl functional groups in the covering film 5, it is more preferable that the main component of the functional groups of the second silicone be methyl functional groups.

In addition to silicone, the coating liquid may contain, for example, solvents, pigments, viscosity modifiers, additives that polymerize silicone, conductive fillers, hollow fillers, and the like.

Additives that polymerize silicone include polymerization initiators and pH adjusters.

Examples of polymerization initiators include polymerization catalysts such as titanium alkoxides and tin compounds.

Examples of pH adjusters include hydrochloric acid and sodium hydroxide.

After the preparation process, the application process is performed.

In the coating step, the coating liquid is applied to the surface 20a of the base material 20. More preferably, the coating amount is such that the film thickness when cured is 60 µm or less.

The application method is not particularly limited. An example of the coating method is spray coating, dip coating, spin coating, brush coating, vacuum deposition, or the like.

After the application process, the curing process is performed.

In the curing step, the coating liquid applied to the surface 20a is heated and cured. The heating method and heating conditions are not particularly limited as long as the polymerization reaction of the silicone in the coating liquid proceeds and the covering film 5 can be formed. For example, it may be heated at a low temperature at which the solvent is volatilized but below the polymerization initiation temperature, and then heated above the polymerization initiation temperature.

The process of forming the covering film 5 on the first gripping portion 2 has been described above. Similarly, the covering film 5 is formed on the surface 30a of the base material 30 to manufacture the second gripping portion 3, and the covering film 5 is formed on the surface 40a of the base material 40 to manufacture the support member 4, respectively.

The wiring 10a is joined to the first gripping portion 2 and the second gripping portion 3, and the first gripping portion 2 and the second gripping portion 3 are fixed to the support member 4 and the holder 9 in such a state that the operating member is connected. In this way, the treatment portion 1 is manufactured.

Next, the action of the treatment portion 1 will be described with a focus on the action of the covering film 5.

For example, the medical energy device 101 can transfer one or both of ultrasonic vibration energy and high-frequency electrical energy to the biological tissue while the biological tissue is sandwiched between the first gripping portion 2 and the second gripping portion 3.

For example, when a drive signal for the piezoelectric element is supplied from the power supply 10 through the wiring 10a, the piezoelectric element ultrasonically vibrates. When the first gripping portion 2 is ultrasonically vibrated, the ultrasonic vibrations are transferred to the biological tissue that contacts the first gripping portion 2. The biological tissue is heated by frictional heat at the contact portion between the first gripping portion 2 and the biological tissue.

For example, a high-frequency current flows from the power supply 10 through the wiring 10a to the biological tissue between the first gripping portion 2 and the second gripping portion 3, so as to generate Joule heat. Thereby, the biological tissue is heated.

In this way, when the biological tissue is heated by one or both of the ultrasonic vibration and the high-frequency current, the water in the biological tissue evaporates rapidly and the proteins in the biological tissue denature. Thereby, the biological tissue is cauterized. When blood is flowing in the biological tissue, the bleeding is stopped at the cauterized portion. When the treatment goal is hemostasis, heating is stopped at the state of hemostasis.

For example, when the purpose of treatment is cutting, heating is continued. The cauterized biological tissue becomes brittle, and the fragile portion is cut by the pressing force from the first gripping portion 2 and the second gripping portion 3.

In order to perform the treatment quickly, it is necessary to raise the temperature of the biological tissue to be treated as high as possible. For example, the temperature of the biological tissue to be treated has conventionally been about 200° C., but it is more preferably 300° C. or higher in order to perform the treatment more quickly. In this case, the temperature of the treatment portion 1 that contacts the biological tissue also reaches 300° C. or higher.

Since the main component of the covering film 5 is a silicone polymer, the covering film 5 as a whole is a solid film containing a three-dimensional network structure due to strong siloxane bonds.

Since the covering film 5 contains 60% or more of methyl functional groups, which have excellent water repellency, in terms of molar ratio as functional groups in silicone, it has excellent adhesion prevention performance to the biological tissue.

Since the siloxane bond has a high thermal decomposition temperature, the covering film 5 has excellent heat resistance. For example, the covering film 5 alone can be used at a temperature of 400° C. or less.

However, the covering film 5 is formed on the base material 20 or the like made of metal, ceramic, or the like having a smaller thermal expansion coefficient than silicone. As the treatment is repeated, the covering film 5 is subjected to repeated thermal stresses due to the difference in thermal expansion coefficients. The higher the temperature of the biological tissue during treatment, the greater the thermal stress.

For this reason, even at temperatures lower than the heat-resistant temperature of silicone, there has been a problem in the past that the silicone deteriorates as the treatment is repeated, and cracks and peeling occur in the covering film of the treated area.

Figure 3:
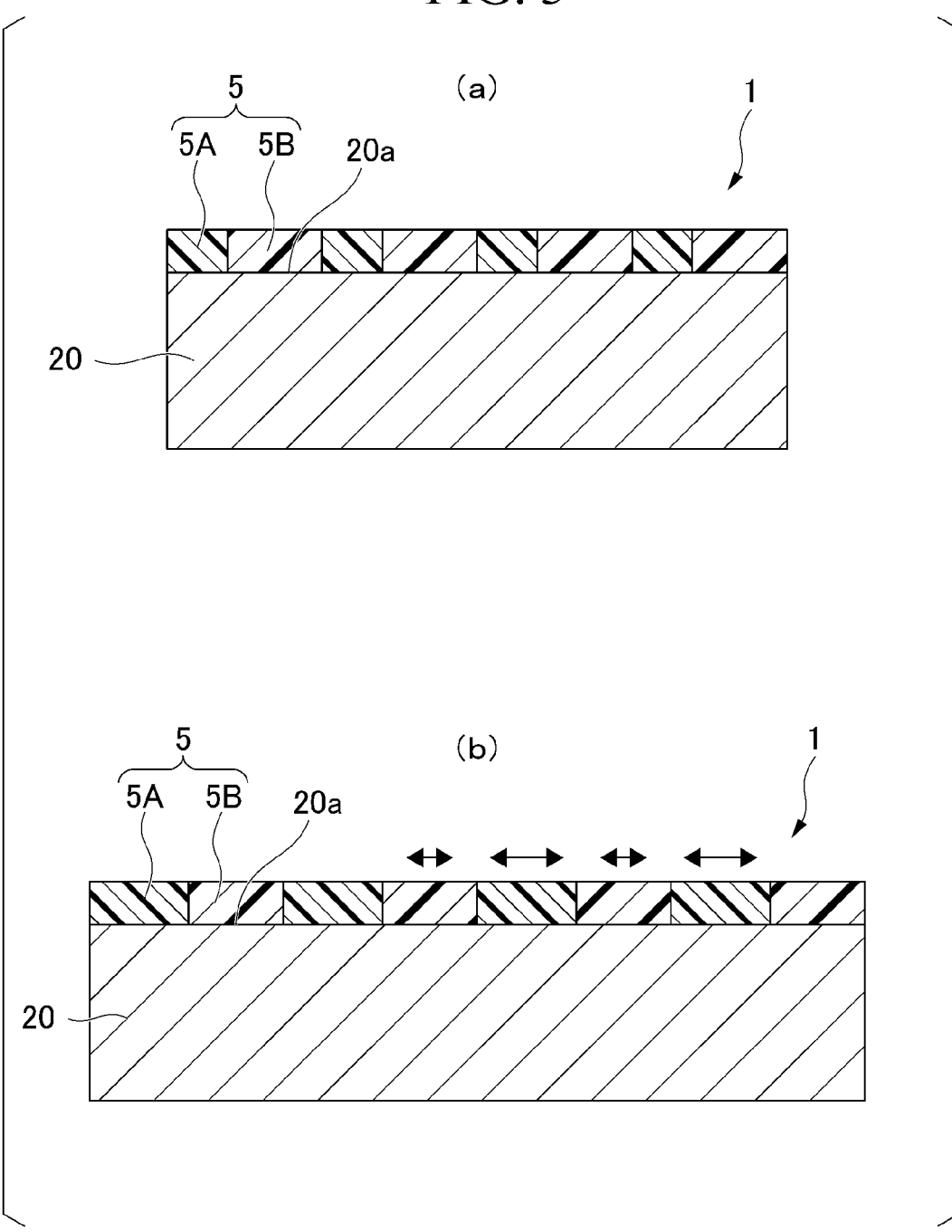
FIG. 3 is a schematic cross-sectional view showing the action of the treatment portion of the medical energy device according to the embodiment of the present invention.

FIG. 3 is a schematic cross-sectional view showing the action of the treatment portion of the medical energy device according to the embodiment of the present invention.

In the present embodiment, the molar ratio of the D unit component in the silicone polymer, which is the main component of the covering film 5, is 40% or more. Thereby, a large number of linear structures in which D units are bonded to each other are formed between parts rich in Q units. Since the linear structure in which the D units are bonded to each other extends in a helical shape, it is superior in stretchability and flexibility as compared with the three-dimensional network structure mainly composed of the Q units.

For this reason, as schematically shown in (a) of FIG. 3, the covering film 5 has a film structure in which a large number of relatively soft portions 5A containing more D units are interposed between a large number of relatively hard portions 5B mainly composed of Q units.

For example, when treatment is performed, the temperature of the treatment portion 1 rises together with the biological tissue to be treated, and the covering film 5 and the base material 20 thermally expand. An internal stress is generated in the covering film 5 due to the difference in thermal expansion coefficient between the silicone of the base material 20 and the covering film 5.

However, as shown schematically in (b) of FIG. 3, the soft portion 5A, which has a higher molar ratio of D units than the hard portion 5B, is easily deformed, and the internal stress is easily buffered. As a result, the internal stress due to the temperature rise is buffered in the covering film 5 as a whole, so cracking and peeling due to repeated thermal stress are suppressed.

The thinner the film thickness of the covering film 5 is, the more the change in internal stress due to repeated thermal expansion is suppressed. Therefore, by making the film thickness of the covering film 5 as thin as possible, the durability of the covering film 5 can be further improved.

As described above, according to the treatment portion 1 and the medical energy device 101 of the present embodiment, durability in repeated treatments can be improved.

In addition, in the description of the above embodiment, an example of a treatment portion used in a medical energy device capable of transferring one or both of ultrasonic vibration and high-frequency electrical energy to the biological tissue has been described. However, the energy used for treating the biological tissue is not limited to this.

For example, the treatment portion may transfer only ultrasonic vibrations or only high-frequency electrical energy to the biological tissue.

For example, the treatment portion may include a heating device such as a heater, and transfer thermal energy generated by the heating device to the biological tissue.

In the description of the above embodiment, the treatment portion has a mechanism for gripping the biological tissue, and an example of gripping the biological tissue and performing treatment has been described. However, the treatment portion may not have a mechanism for gripping the biological tissue. In this case, for example, the treatment portion may be formed in a rod-like or plate-like shape that allows treatment by being pressed against the biological tissue.

In the description of the above embodiment, an example in which the shape of the first gripping surface 2a and the second gripping surface 3a is a combination of flat planes has been described. However, the surface of the base material covered by the covering film may be, for example, a flat surface, a curved surface, or the like. The surface of the base material covered with the covering film may be, for example, an uneven surface having a smaller amount of unevenness than the film thickness.

In the description of the above embodiment, an example in which the same covering film 5 is formed on the entire surfaces of the first gripping portion 2, the second gripping portion 3, and the support member 4 in the treatment portion 1 has been described.

However, the composition, film thickness, and the like of the covering film 5 may be appropriately changed according to the temperature of each surface of the treatment portion 1, the possibility of contact with the biological tissue, and the like.

In particular, the support member 4 is less likely to be pressed by the body to be treated during use, compared to the first gripping portion 2 and the second gripping portion 3. Furthermore, the temperature of the support member 4 may be lower than that of the first gripping portion 2 and the second gripping portion 3. Therefore, the support member 4 may have lower mechanical strength, heat resistance, and the biological tissue adhesion prevention than the first gripping portion 2 and the second gripping portion 3 in some cases.

Similarly, in the first gripping portion 2 and the second gripping portion 3, the material and thickness of the covering film 5 on the first gripping surface 2a and the second gripping surface 3a may be different from the composition and thickness of the covering film 5 on the outer surfaces 2b and 3b.

Furthermore, in the treatment portion 1, the covering film 5 may not be formed on surfaces that are less likely to come into contact with the biological tissue or that have a low temperature. That is, the covering film 5 mainly composed of silicone having a D unit component molar ratio of 40% or more and a methyl functional group molar ratio of 60% or more may be formed at least on the surface region of the treatment portion 1 that comes into contact with the biological tissue. In the treatment portion 1, the main body portion may be exposed in the surface region other than that covered with the covering film 5, or another covering film that does not correspond to the covering film 5 may be formed.

EXAMPLES

Next, Examples 1 to 5 relating to the embodiment will be described along with Comparative Examples 1 and 2. The following Table 1 shows the components of the coating liquid, the structure of the covering film, and the evaluation results in Examples 1 to 5 and Comparative Examples 1 and 2.

Example 1

Example 1 is an example corresponding to the treatment portion 1 described above.

In Example 1, the base materials 20, 30, and 40 formed in the shapes of the first gripping portion 2, the second gripping portion 3, and the support member 4, and a coating liquid for forming the covering film 5 are prepared.

SUS304, which is stainless steel, was used as the material for the base materials 20, 30, and 40.

As shown in Table 1, the coating liquid was prepared containing a first silicone, a second silicone, and a polymerization initiator.

The reason why the first silicone and the second silicone are mixed is that by changing the compounding ratio of each, it is possible to easily prepare coating liquids used in other examples with different D unit molar ratios.

A polydiorganosiloxane having a D unit component molar ratio of 100% was used as the first silicone. All the functional groups of the first silicone were methyl functional groups (described as "methyl" in Table 1). The content of the first silicone was 100 parts by mass.

As the second silicone, a methyl/phenyl silicone resin having a T unit component molar ratio of 100% and containing a methyl functional group and a phenyl group as functional groups ("functional group" in Table 1 is "methyl/phenyl" described) was used. The content of the second silicone was 80 parts by mass.

As a polymerization initiator, 15 parts by mass of titanium alkoxide, which is a polymerization catalyst, was added.

After that, the coating liquid was applied to the surfaces of the base materials 20, 30, and 40 by spray coating. The coating amount was adjusted so that the film thickness when cured became 80 μm.

After that, the base materials 20, 30, and 40 with the covering film formed thereon were heated in a drying oven adjusted to 80° C. for 30 minutes to temporarily harden the covering film. After that, the base materials 20, 30, and 40 with the covering film formed thereon were heated in a drying oven adjusted to 240° C. for 1 hour. As a result, the polymerization of the first silicone and the second silicone proceeded to form a covering film 5 having a thickness of 80 μm.

TABLE 1

| | COMPONENT OF COATING LIQUID | | | | | COVERING FILM | | | | |
| | FIRST SILICONE | | SECOND SILICONE | | POLYMER-IZATION INITIATOR | FILM | D UNIT SILICONE | METHYL FUNC-TIONAL GROUP | EVALUATION | |
| | PARTS BY MASS | FUNC-TIONAL GROUP | PARTS BY MASS | FUNC-TIONAL GROUP | PARTS BY MASS | THICK-NESS (μm) | MOLAR RATIO (%) | MOLAR RATIO (%) | INCISION NUMBER (TIMES) | DETER-MINA-TION |
|---|---|---|---|---|---|---|---|---|---|---|
| EXAMPLE 1 | 100 | METHYL | 80 | METHYL/PHENYL | 15 | 80 | 50 | 67 | 50 | A |
| EXAMPLE 2 | 100 | METHYL | 40 | METHYL/PHENYL | 15 | 80 | 73 | 84 | 60 | A |
| EXAMPLE 3 | 100 | METHYL | 40 | METHYL | 15 | 80 | 73 | 100 | 80 | A |
| EXAMPLE 4 | 100 | METHYL | 40 | METHYL | 15 | 20 | 73 | 100 | 90 | A |
| EXAMPLE 5 | 100 | METHYL | 105 | METHYL | 15 | 20 | 43 | 60 | 70 | A |
| COMPARATIVE EXAMPLE 1 | 100 | METHYL | 200 | METHYL | 15 | 80 | 29 | 100 | 20 | B |
| COMPARATIVE EXAMPLE 2 | 100 | PHENYL | 80 | METHYL | 15 | 80 | 50 | 33 | 10 | B |

The treatment portion 1 of Example 1 was manufactured by assembling the first gripping portion 2, the second gripping portion 3, and the support member 4.

Examples 2 to 5

In the following, Examples 2 to 5 will be described, focusing on the differences from Example 1 and the like.

In Example 2, the same covering film 5 as in Example 1 was formed, except that the second silicone in the coating liquid was 40 parts by mass.

In Example 3, the covering film 5 was formed in the same manner as in Example 2, except that the functional groups of the second silicone in the coating liquid were all methyl functional groups.

In Example 4, the covering film 5 was formed in the same manner as in Example 3 except that the film thickness was changed to 20 μm by changing the coating amount of the coating liquid.

In Example 5, the same covering film 5 as in Example 4 was formed, except that the amount of the second silicone in the coating liquid was 105 parts by mass.

Comparative Examples 1 and 2

In Comparative Example 1, the same covering film as in Example 3 was formed, except that the second silicone in the coating liquid was 200 parts by mass.

In Comparative Example 2, the same covering film as in Example 1 was formed, except that the functional groups of the first silicone in the coating liquid are all phenyl groups, and the functional groups of the second silicone were all methyl functional groups.

[Evaluation of Covering Film]

The D unit component molar ratio (described in Table 1 as "D unit silicon molar ratio") and the molar ratio of methyl functional groups (described in Table 1 as "methyl functional group molar ratio") of each covering film of each example and each comparative example were measured.

As a method for quantifying the D unit component molar ratio, the solid $^{29}$Si-NMR method using a nuclear magnetic resonance apparatus JNM-ECA400 (trade name; manufactured by JEOL Ltd.) was used. Specifically, a $^{29}$Si-NMR spectrum was obtained and analyzed, and the D unit component molar ratio was quantified as the ratio of the D unit peak area to the total peak area.

As a method for quantifying the methyl functional group molar ratio, the solid $^{13}$C-NMR method using JNM-ECA400 and the solid $^{1}$H-NMR method were used in combination. Specifically, a $^{13}$C-NMR spectrum and a $^{1}$H-NMR spectrum were obtained and analyzed, and the methyl functional group molar ratio was quantified as the ratio of the peak area of the methyl functional group to the peak area of all functional groups bonded to the silicon atom.

[Evaluation of Treatment Performance]

Each treatment portion of each example and each comparative example was assembled as a medical energy device, and then subjected to a bio-tissue incision treatment test.

As the body tissue to be treated, pig blood vessels were used.

A single incision operation was performed by gripping the pig's blood vessel with a force of 2 N and holding it for 3 seconds. At that time, the relationship between the oscillation pattern of the ultrasonic vibration and the high-frequency power and the temperature of the covering film was examined in advance, and a signal based on the oscillation pattern was applied so that the temperature of the covering film become 300° C.

The above-described incision was repeated every 5 seconds on the body to be treated. At the end of each incision operation, it was evaluated whether or not the blood vessel had been cut and whether or not the biological tissue had adhered to the treated area.

The number of incisions was recorded as the number of incisions until the biological tissue adhered to the treated area and the blood vessels were no longer cut apart (see Table 1). In each example and each comparative example, there was no example in which adhesion of the biological tissue was not observed when the blood vessel was not cut. Therefore, it is considered that the deterioration of the incision performance of the treatment portion is caused by the adhesion of the biological tissue.

A case where the number of incisions was 50 or more is defined as "good" (described as "A" in Table 1). A case where the number of incisions was less than 50 is defined as "not good" (described as "B" in Table 1).

[Evaluation Results]

As shown in Table 1, the D unit component molar ratios in Examples 1 to 5 were 50%, 73%, 73%, 73% and 43%, respectively. The molar ratios of methyl functional groups in Examples 1 to 5 were 67%, 84%, 100%, 100% and 60%, respectively.

On the other hand, the D unit component molar ratios in Comparative Examples 1 and 2 were 29% and 50%, respectively. The molar ratios of methyl functional groups in Comparative Examples 1 and 2 were 100% and 33%, respectively.

The number of incisions in Examples 1 to 5 were 50, 60, 80, 90, and 70, respectively.

On the other hand, the number of incisions in Comparative Examples 1 and 2 were 20 and 10, respectively.

From the above evaluation results, the covering films 5 of Examples 1 to 5 all had the D unit component molar ratio of 40% or more and 99% or less, and the methyl functional group molar ratio of 60% or more.

All of the incision performances of Examples 1 to 5 were judged to be "good."

When the film thickness was the same, the greater the D unit component molar ratio and the methyl functional group molar ratio, the greater the number of incisions. For example, when Examples 2 and 3 were compared, when the film thickness and D unit molar ratio were the same, the number of incisions was greater in Example 3, which had a higher methyl functional group molar ratio.

For example, when comparing Examples 3 and 4, when the D unit component molar ratio and the methyl functional group molar ratio were the same, the number of incisions was greater in Example 4, which had a smaller film thickness.

For example, when comparing Examples 1 and 5, even though the D unit component molar ratio and the methyl functional group molar ratio were smaller than those of Example 1, Example 5, which had a smaller film thickness, had a larger number of incisions.

When the film thickness was thin, the internal stress generated in the covering film 5 was low, so cracks and the like in the covering film were less likely to occur, and it is thought that the incision performance had been improved.

On the other hand, both Comparative Examples 1 and 2 were determined to be "not good".

In the case of Comparative Example 1, the film thickness and the methyl functional group molar ratio were the same as in Example 3, but the D unit component molar ratio was less than 40%, so the number of incisions was significantly reduced.

In Comparative Example 1, the anti-adhesion effect of methyl functional groups was the same as in Example 3. However, it is believed that there are too few D units, resulting in poor stretchability and flexibility of the coating. For this reason, it is considered that repeated incisions cause cracks in the covering film, and increased biological tissue adheres to the cracks, resulting in a decrease in incision performance.

In the case of Comparative Example 2, the film thickness and D unit component molar ratio were the same as in Example 1, but the methyl functional group molar ratio was less than 60%, so the number of incisions was significantly reduced.

Comparative Example 2 had elasticity to some extent depending on the molar ratio of the D unit component. However, it is considered that the anti-adhesion performance was lowered because the water repellency of the surface of the covering film is insufficient.

Next, Examples 6 to 9 relating to the embodiment will be described along with Comparative Examples 3 to 5. Examples 6 to 9 and Comparative Examples 3 to 5 are examples and comparative examples in which the covering film 5 contained hollow fillers. The evaluations by Examples 6 to 9 and Comparative Examples 3 to 5 were intended to evaluate the heat insulation performance of covering films containing hollow fillers.

Below, the points different from the first embodiment will be mainly described.

The following Table 2 shows the components of the coating liquid, the structure of the covering film, and the evaluation results in Examples 6 to 9 and Comparative Example 3.

Regarding the evaluation of the durability of the covering film, although not shown in particular, Examples 6 to 9 and Comparative Example 3, in which the D unit component molar ratio was 40% or more and 99% or less and methyl functional group molar ratio was 60% or more, all showed good performance.

Examples 6 to 9

In Example 6, the covering film 5 was formed in the same manner as in Example 1 except that the second silicone was 50 parts by mass, the functional groups of the first silicone were all methyl functional groups, all the functional groups of the second silicone were all methyl functional groups, and the hollow filler was formed by the coating liquid added with 10 parts by mass. However, the covering film 5 in Examples 6 to 9 was formed on a part where the biological tissue was not gripped during treatment, such as the outer surface 2b of the first gripping portion 2 and the outer surface 3b of the second gripping portion 3, for example.

As the material for the hollow filler, an alumina-borosilicate glass-based inorganic material was used.

In Example 7, the same covering film 5 as in Example 6 was formed, except that the film thickness was 100 μm.

In Example 8, the covering film 5 was formed in the same manner as in Example 6, except that the second silicone was formed from a coating liquid containing 80 parts by mass.

In Example 9, the same covering film as in Example 8 was formed, except that the hollow filler in the coating liquid was 45 parts by mass.

Comparative Example 3

In Comparative Example 3, the same covering film as in Example 7 was formed, except that the hollow filler in the coating liquid was 5 parts by mass.

Comparative Example 4

In Comparative Example 4, the same covering film as in Example 7 was formed, except that the second silicone in the coating liquid was 200 parts by mass.

Comparative Example 5

In Comparative Example 5, the same covering film as in Comparative Example 4 was formed, except that the hollow filler in the coating liquid was 50 parts by mass. However,

TABLE 2

| | COMPONENT OF COATING LIQUID | | | | | | COVERING FILM | | | | |
| | FIRST SILICONE | | SECOND SILICONE | | POLYMER-IZATION AGENT | HOLLOW FILLER | FILM | D UNIT | METHYL FUNC-TIONAL GROUP | VA-CAN-CY RATE | EVALUATION | |
| | | | | | | | | | | | RATIO OF | |
| | PARTS BY MASS | FUNC-TIONAL GROUP | PARTS BY MASS | FUNC-TIONAL GROUP | PARTS BY MASS | PARTS BY MASS | THICK-NESS (μm) | SILICONE MOLAR (%) | MOLAR RATIO (%) | RATE (%) | WHITENED AREA (%) | DETER-MINA-TION |
| EXAMPLE 6 | 100 | METHYL | 50 | METHYL | 15 | 10 | 80 | 62 | 100 | 20 | 9 | A+ |
| EXAMPLE 7 | 100 | METHYL | 50 | METHYL | 15 | 10 | 100 | 62 | 100 | 20 | 5 | A+ |
| EXAMPLE 8 | 100 | METHYL | 80 | METHYL | 15 | 10 | 80 | 50 | 100 | 20 | 50 | A |
| EXAMPLE 9 | 100 | METHYL | 80 | METHYL | 15 | 45 | 80 | 50 | 100 | 90 | 2 | A+ |
| COMPARA-TIVE EXAMPLE 3 | 100 | METHYL | 50 | METHYL | 15 | 5 | 100 | 62 | 100 | 10 | 80 | B |
| COMPARA-TIVE EXAMPLE 4 | 100 | METHYL | 200 | METHYL | 15 | 10 | 100 | 30 | 100 | 20 | 80 | B |
| COMPARA-TIVE EXAMPLE 5 | 100 | METHYL | 200 | METHYL | 15 | 50 | 100 | 30 | 100 | 95 | — | B | in Comparative Example 5, the covering film peeled off immediately after the film was formed.

[Evaluation of Covering Film]

The D unit component molar ratio (described in Table 2 as "D unit silicon molar ratio") and the molar ratio of methyl functional groups (described in Table 2 as "methyl functional group molar ratio") were measured in the same manner as in Example 1.

Furthermore, using a scanning electron microscope ERA-600FE (trade name: manufactured by Elionix Co., Ltd.), the cross section of each covering film of Examples 6-9 and Comparative Examples 3-5 was observed to measure the vacancy rate.

Examples 6 to 9 and Comparative Examples 3 to 5 are intended to evaluate the heat insulation performance of covering films containing hollow fillers, so quantitative evaluation of treatment performance was omitted. However, when incision was performed according to Examples 6 to 9 and Comparative Example 3, even if hollow fillers were contained, the treatment performance showed performance depending on the D unit component molar ratio.

[Evaluation of Thermal Insulation Performance]

After each treatment portion of Examples 6 to 8 and Comparative Examples 3 and 4 was assembled as a medical energy device, for the purpose of evaluating the heat insulation performance of the covering film, the heat insulation performance test of the treatment portion were performed as follows.

First, ultrasonic vibration and high-frequency power were oscillated so that the surface of the treatment portion reached 300° C., and then the temperature was returned to normal temperature, which was repeated 500 times. Thereafter, after oscillating again so that the surface of the treatment portion reached 300° C., immediately after stopping the oscillation, the outer surface of the treatment portion not gripping the biological tissue, specifically, the back portion of the outer surface facing the gripping surface was pressed against the pig liver with a force of 2N for 3 seconds.

After that, the surface area of the whitened part on the surface (pressing surface) of the pig liver to which the back portion was pressed was measured, and the ratio of the surface area of the whitened part to the total area of the pressing surface (ratio of whitened area) was obtained.

A case where the ratio of the whitened area was 10% or less is referred to as "very good" (described as "A+" in Table 2), a case where it was more than 10% and 60% or less is referred to as "good" (described as "A" in Table 2), and a case where it exceeded 60% is defined as "not good" (described as "B" in Table 2).

[Evaluation Results]

As shown in Table 2, the D unit component molar ratios in Examples 6 to 9 were 62%, 62%, 50% and 50%, respectively. The methyl functional group molar ratios in Examples 6 to 9 were all 100%.

In contrast, the D unit component molar ratios in Comparative Examples 3 to 5 were 62%, 30%, and 30%, respectively. The molar ratios of methyl functional groups in Comparative Examples 3-5 were all 100%.

The hollow ratios of the coating membranes 5 in Examples 6 to 9 were 20%, 20%, 20% and 90%, respectively.

On the other hand, the hollow ratios of the coating membranes in Comparative Examples 3 to 5 were 10%, 20%, and 95%, respectively.

The ratios of whitened areas in Examples 6 to 9 were 9%, 5%, 50%, and 2%, respectively. Therefore, the heat insulation performance of Examples 6, 7 and 9 was judged to be "very good", and the heat insulation performance of Example 8 was judged to be "good".

On the other hand, the ratio of whitened area in Comparative Examples 3 and 4 was 80%. Therefore, the thermal insulation performance of Comparative Examples 3 and 4 was determined to be "not good".

In Comparative Example 5, since the covering film had peeled off before the start of the evaluation, the whitened area could not be evaluated. Therefore, the heat insulation performance was also determined to be "not good".

From the above evaluation results, the covering films 5 of Examples 6 to 9 all had a D unit component molar ratio of 40% or more and 99% or less, and a methyl functional group molar ratio of 60% or more.

With regard to heat insulation performance, in Examples 6 to 9, in which the hollow ratio of the covering film was 20% or more and 90% or less, the whitened area was judged to be "very good" or "good".

The coating membranes 5 of Examples 6 to 9 had good heat insulation properties, so the heat transfer to the pig liver through the coating membrane was low, and the percentage of whitened area was small.

On the other hand, in Comparative Example 3, since the vacancy rate of the covering film was as low as 10%, the heat insulation performance was low, and the whitened area was judged to be "not good".

In Comparative Example 4, the vacancy rate of the covering film was 20%, but the whitened area was determined to be "not good". The reason for this is that the molar ratio of silicon in the D unit was as low as 30%, so that the durability of the covering film was low and the covering film was destroyed.

It was found that when the vacancy rate of the covering film 5 was 20% or more and 90% or less, the heat insulation performance of the covering film 5 was improved, so that heat transfer to the biological tissue was reduced, and damage to the biological tissue could be suppressed.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

According to the above embodiments, it is possible to provide a treatment portion of a medical energy device, a manufacturing method thereof, and a medical energy device capable of improving durability in repeated treatments.

What is claimed is:

1. A treatment portion of a medical energy device that treats a biological tissue by transferring energy to the biological tissue, in a state where the treatment portion is in contact with the biological tissue, the treatment portion comprising:

a main body portion that transfers the energy to the biological tissue; and a covering film that contains silicone as a main component and covers a surface of the main body portion, wherein the silicone includes at least a D unit and a T unit, in the silicone, a molar ratio of silicon atoms forming the D unit with respect to all the silicon atoms is 40% or more and 99% or less, and in the silicone, a molar ratio of methyl functional groups bonded to the silicon atoms with respect to all functional groups bonded to the silicon atoms is 60% or more, and wherein the covering film has a film structure in which relatively soft portions comprising the silicone are interposed between relatively hard portions comprising a second silicone mainly composed of Q units, with the relatively soft portions containing a higher molar ratio of D units than the relatively hard portions.

2. The treatment portion of the medical energy device according to claim 1, wherein, in the silicone, the molar ratio of the silicon atoms forming the D unit with respect to all the silicon atoms is 60% or more and 99% or less.

3. The treatment portion of the medical energy device according to claim 1, wherein, in the silicone, the molar ratio of the methyl functional groups bonded to the silicon atoms with respect to all the functional groups is 90% or more.

4. The treatment portion of the medical energy device according to claim 1, wherein a film thickness of the covering film is 60 μm or less.

5. The treatment portion of the medical energy device according to claim 1, wherein the covering film contains a conductive filler.

6. The treatment portion of the medical energy device according to claim 5, wherein the covering film contains the conductive filler at a volume ratio of 40% or more and 90% or less.

7. The treatment portion of the medical energy device according to claim 1, wherein a vacancy rate of the covering film is 20% or more and 90% or less.

8. The treatment portion of the medical energy device according to claim 7, wherein a film thickness of the covering film is 50 μm or more.

9. A medical energy device comprising a treatment portion that treats a biological tissue by transferring energy to the biological tissue, in a state where the treatment portion is in contact with the biological tissue, the treatment portion comprising:

a main body portion that transfers the energy to the biological tissue; and a covering film that contains silicone as a main component and covers a surface of the main body portion, wherein the silicone includes at least a D unit, and wherein in the silicone, a molar ratio of silicon atoms forming the D unit with respect to all the silicon atoms is 40% or more and 99% or less, and wherein in the silicone, a molar ratio of methyl functional groups bonded to the silicon atoms with respect to all functional groups bonded to silicon atoms is 60% or more, and wherein the covering film has a film structure in which relatively soft portions comprising the silicone are interposed between relatively hard portions comprising a second silicone mainly composed of Q units, with the relatively soft portions containing a higher molar ratio of D units than the relatively hard.

10. A manufacturing method for a treatment portion of a medical energy device that treats a biological tissue by transferring energy to the biological tissue, in a state where the treatment portion is in contact with the biological tissue, the method comprising:

preparing a main body portion and a coating liquid, the main body portion being for transferring the energy to the biological tissue, the coating liquid containing silicone including at least a D unit and a T unit and being a polymer in which a molar ratio of silicon atoms forming the D unit with respect to all the silicon atoms is 40% or more and 99% or less, and a molar ratio of methyl functional groups bonded to the silicon atoms with respect to all functional groups bonded to the silicon atoms is 60% or more;

applying the coating liquid to a surface of the main body portion; and forming a covering film which contains the silicone as a main component and covers the surface of the main body portion by heating and curing the applied coating liquid and wherein the covering film has a film structure in which relatively soft portions comprising the silicone are interposed between relatively hard portions comprising a second silicone mainly composed of Q units, with the relatively soft portions containing a higher molar ratio of D units than the relatively hard.

* * * * *